United States Patent
Rich

(10) Patent No.: US 6,355,410 B1
(45) Date of Patent: Mar. 12, 2002

(54) METHOD OF REDUCING CELL PROLIFERATION BY INHIBITING THE NA⁺/H⁺ EXCHANGER AND INDUCING APOPTOSIS

(76) Inventor: Ivan N Rich, 213 Williamstown Way, Columbia, SC (US) 29212

( * ) Notice: Subject to any disclaimer, the term of this patent is extended or adjusted under 35 U.S.C. 154(b) by 0 days.

(21) Appl. No.: 09/325,444

(22) Filed: Jun. 3, 1999

Related U.S. Application Data

(60) Provisional application No. 60/087,864, filed on Jun. 3, 1998.

(51) Int. Cl.⁷ .......................... G01N 1/28; G01N 33/48; G01N 33/483; G01N 33/53; G01N 33/574

(52) U.S. Cl. .................... 435/2; 435/4; 435/6; 435/7.1; 435/7.21; 435/7.23; 435/7.24; 435/325; 435/363; 435/366; 435/372; 435/372.1; 435/372.2; 435/372.3; 435/375

(58) Field of Search .............................. 436/813, 824, 436/63; 435/7.2, 7.23, 7.24, 325, 6, 372.1, 7.1, 2, 4, 363, 366, 372.3, 375, 372.2, 7.21

(56) References Cited

U.S. PATENT DOCUMENTS 5,523,286 A * 6/1996 McGlave et al.

OTHER PUBLICATIONS

Noguchi 1991. Use of Flow Cytometry for DNA Analysis. In Current Protocols in Immunology (J.E. Colligan et al, eds) pp 5.7.1–5.7.6. Greene Publishing and Wiley–Interscience, New York.*
Reynolds et al. Cytometry 25:349–357 1996.*
van Erp et al. Cytometry 12;127–132 1991.*
Shapiro 1995. In Practical Flow Cytometry. Published by Wiley–Liss, New York. Chpt 6 p 217; Chpt 7 pp 229–230, 244–245, 326, 345–348; Chpt 10 pp 367, 388–391.*
"Intracellular pH measurements in Ehrlich ascites tumor cells utilizing spectroscopic probes generated in situ"; JA Thomas, RN Buchsbaum, A. Zimniak, E. Racker; Biochemistry 18, 2210–2218; 1979.
"A specific mutation abolishing Na⁺/H⁺ antiport activity in hamster fibroblasts precludes growth at neutral and acidic pH"; J. Pouyssegur, C. Sardet, A. Franchi, G. L'Allemain, S. Paris; Proc. Natl. Acad. Sci. U.S.A. 81, 4833–4837; 1984.
"Interleukin–3–stimulated haemopoietic stem cell proliferation. Evidence for activation of protein kinase C and Na⁺/H⁺ exchange without inositol lipid hydrolysis"; AD Whetton et al.; Biochem. J. 256, 585–592; 1988.
"Amiloride and its analogs as tools in the study of ion transport"; TR Kleyman, EJ Cragoe; J. Membrane Biol. 105, 1–21; 1988.
"Requirement of the Na⁺/H⁺ exchanger for tumor growth"; D. Rotin, D. Steele–Norwood, S. Grinstein, I. Tannock; Cancer Res. 49, 205–211; 1989.

"Cloning of the human genomic amiloride–sensitive Na+/H+ antiporter gene, identification of genetic polymorphisms, and localization on the genetic map of chromosome 1p"; RP Lifton, C. Sardet, J. Pouyssegur, JM Lalouel; Genomics 7, 131–135; 1990.
"Granulocyte–macrophage colony–stimulating factor can stimulate macrophage proliferation via persistent activation of Na⁺/H⁺ antiport. Evidence for two distinct roles for Na+/H+ antiport activation"; SJ Vallance, CP Downes, EJ Cragoe, AD Whetton; Biochem. J. 265, 359–364; 1990.
"The Na⁺/H⁺ antiporter in oncology in the light of the spontaneous regression of cancer and cell metabolism"; S. Harguindey, EJ Cragoe; Med. Hypotheses 39, 229–237; 1992.
"The Na⁺/H⁺ exchanger: an update on structure, regulation and cardiac physiology"; L. Fliegel, O. Frohlich; Biochem. J. 296, 273–285; 1993.
"Antitumor activity of nigericin and 5–(N–ethyl–N–isopropyl)amiloride: an approach to therapy based on cellular acidification and the inhibition of regulation of intracellular pH", K. Hasuda, C. Lee, IF Tannock; Oncol. Res. 6, 259–268; 1994.
"Apoptosis in an interleukin–2–dependent cytotoxic T lymphocyte cell line is associated with intracellular acidification. Role of the Na(+)/H(+)–antiporter"; J. Li, A. Eastman, J. Biol. Chem. 270, 3203–3211; 1995.
"Intracellular alkalinization suppresses lovastatin–induced apoptosis in HL–60 cells through the inactivation of the pH–dependent endonuclease"; D. Perez–Sala, D. Collado–Escobar, F. Mollinedo; J. Biol. Chem. 270, 6235–6242; 1995.
"Apoptosis induced by IL–2 withdrawal is associated with an intracellular acidification"; A. Rebollo et al.; Exp. Cell. Res. 218, 581–585; 1995.
"Growth pattern and clinical correlation of subcutaneously inoculated human primary acute leukemias in severe combined immunodeficiency mice"; Y. Yan et al.; Blood 88, 3137–3146; 1996.
"The relationship between thermosensitively and intracellular pH in cells deficient in Na⁺/H⁺ antiport function"; FF Liu, D. Diep, RP Hill; Radiother. Oncol. 40, 75–78; 1996.

(List continued on next page.)

*Primary Examiner*—Philip Gambel
*Assistant Examiner*—Jessica H. Roark
(74) *Attorney, Agent, or Firm*—Womble Carlyle Sandridge & Rice PLLC

(57) ABSTRACT

The Na⁺/H⁺ exchanger isoform 1 (NHE-1) is primarily responsible for the regulation of the intracellular pH ($pH_i$). It is a ubiquitous amiloride-sensitive growth factor activatable exchanger. There is a direct correlation between the $pH_i$ and cell cycle status of normal hemopoietic and leukemic cells, with leukemic cells having a higher $pH_i$ than normal hemopoietic cells. A method is provided to sort cells by flow cytometry into subpopulations of proliferating and non-proliferating cells and to induce apoptosis in proliferating leukemic cells by inhibiting the Na+/H+ exchanger, thereby lowering the internal $pH_i$.

5 Claims, 10 Drawing Sheets

OTHER PUBLICATIONS

"Activation of the Na(+)/H(+) antiporter, Na+/HCO3(–)/CO3(2—) cotransporter, or Cl(—)/HCO3(—) exchanger in spontaneous thymocyte apoptosis"; N. Tsao, HY Lei; J. Immunol. 157, 1107–1116; 1996.

"Molecular physiology of vertebrate $Na^+/H^+$ exchangers"; S. Wakabayashi, M. Shigekawa, J. Pouyssegur; Physiol. Rev. 77, 51–74; 1997.

"Acid pH in tumors and its potential for therapeutic exploitation"; IF Tannock, D. Rotin; Cancer Res. 49, 4373–4384; 1997.

"Tumor cell proliferation is abolished by inhibitors of $Na^+/H^+$ and HCO3/Cl exchange"; B. Horvat, S. Taheri, A. Salihagic; Eur. J. Cancer 1992 29 A, 132–137; 1997.

"Role of acid/base homestasis in the suppression of apoptosis in haemopoietic cells by v–Abl protein tyrosine kinase"; Q. Chen et al.; J. Cell Sci. 110, 379–387; 1997.

"Activation of the sodium/hydrogen exchanger via the fibronectin–integrin pathway results in hematopoietic stimulation"; IN Rich, I. Brackman, D. Worthington–White, MJ Dewey; J. Cell. Physiol. 177, 109–122; 1998.

* cited by examiner

METHOD OF REDUCING CELL PROLIFERATION BY INHIBITING THE NA⁺/H⁺ EXCHANGER AND INDUCING APOPTOSIS

PRIORITY CLAIM

The applicant claims the benefit of the filing date of a U.S. provisional application, Ser. No. 60/087,864, filed Jun. 3, 1998, which is hereby incorporated by reference.

FIELD OF THE INVENTION

The present invention relates generally to treatment of patients with leukemia. In particular, the present invention relates to the apoptosis of leukaemic cells.

BACKGROUND OF THE INVENTION

The ubiquitous, amiloride-sensitive, growth factor activatable sodium/hydrogen exchanger isoform 1 (NHE-1) represents one of the primary mechanisms by which cells regulate intracellular pH (pH$_i$) (1, 2). The human NHE-1 is an 815 amino acid membrane protein transporter produced from the 70 kb long APNH gene on chromosome 1 (3). The protein has 12 membrane spanning segments containing the amiloride-binding site and the highly conserved Na⁺/H⁺ binding site. The cytoplasmic domain contains the pH sensor and maintenance sites (2). It also contains regions which activate the antiporter when growth factors, mitogens or non-mitogenic signals act on the cell (2). Activation of NHE-1 results in a 1:1 efflux of H⁺ and influx of Na⁺ ions, with a concomitant increase in pH$_i$. Increased pH$_i$ is associated with cell stimulation and proliferation (1). Using the interleukin-3 (IL-3)-dependent stem cell line, FDCP-mix, Whetton et al (4) demonstrated that IL-3 activated the NHE and that the resulting intracellular alkalinization was a signal for proliferation of these cells. When granulocyte-macrophage colony-stimulating factor (GM-CSF) was used to stimulate macrophage proliferation, activation of the NHE was detected (5). Removal of growth factors such as IL-2 from IL-2 dependent cytotoxic T cells resulted in a decrease in pH$_i$ and the onset of apoptosis (6, 7). We have demonstrated that murine bone marrow cells could be stimulated by interaction of the $\alpha_4$ integrin subunit with fibronectin, in the absence of growth factors, causing activation of NHE-1, an increase in pH$_i$ and increased colony formation of hemopoietic stem and progenitor cells (8). Several reports using different leukemic cell lines demonstrated that if the Na⁺/H⁺ exchanger was inhibited by amiloride analogues, acidification of the cells occurred with induction of apoptosis (9–11). We hypothesize that cells maintaining a high rate of proliferation should exhibit a sustained increase in pH$_i$ relative to normal cells as a result of activation of the sodium/hydrogen exchanger. Here we show that leukemia cell lines and primary patient leukemic samples exhibit a greater pH$_i$ than normal cells, that pH$_i$ is correlated with cell cycle status and that inhibition of NHE-1 in leukemic patient samples results in a decrease in pH$_i$ and increase in apoptosis. We therefore demonstrate that an inhibitor of NHE-1 has anti-leukemic activity.

SUMMARY OF THE INVENTION

A method is provided to sort cells by flow cytometry into subpopulations of proliferating and non-proliferating cells and to induce apoptosis in proliferating hemopoietic and leukemic cells by inhibiting the Na⁺/H⁺ exchanger, thereby lowering the internal pH.

BRIEF DESCRIPTION OF THE DRAWINGS

FIG. 5A illustrates Fluorescence Ratio Imaging Microscopy; FIG. 5B illustrates Flow Cytometry; FIG. 5C illustrates Annexin-V-FITC; FIG. 5D illustrates TUNEL assays.

DETAILED DESCRIPTION OF PREFERRED EMBODIMENTS

Figure 1:
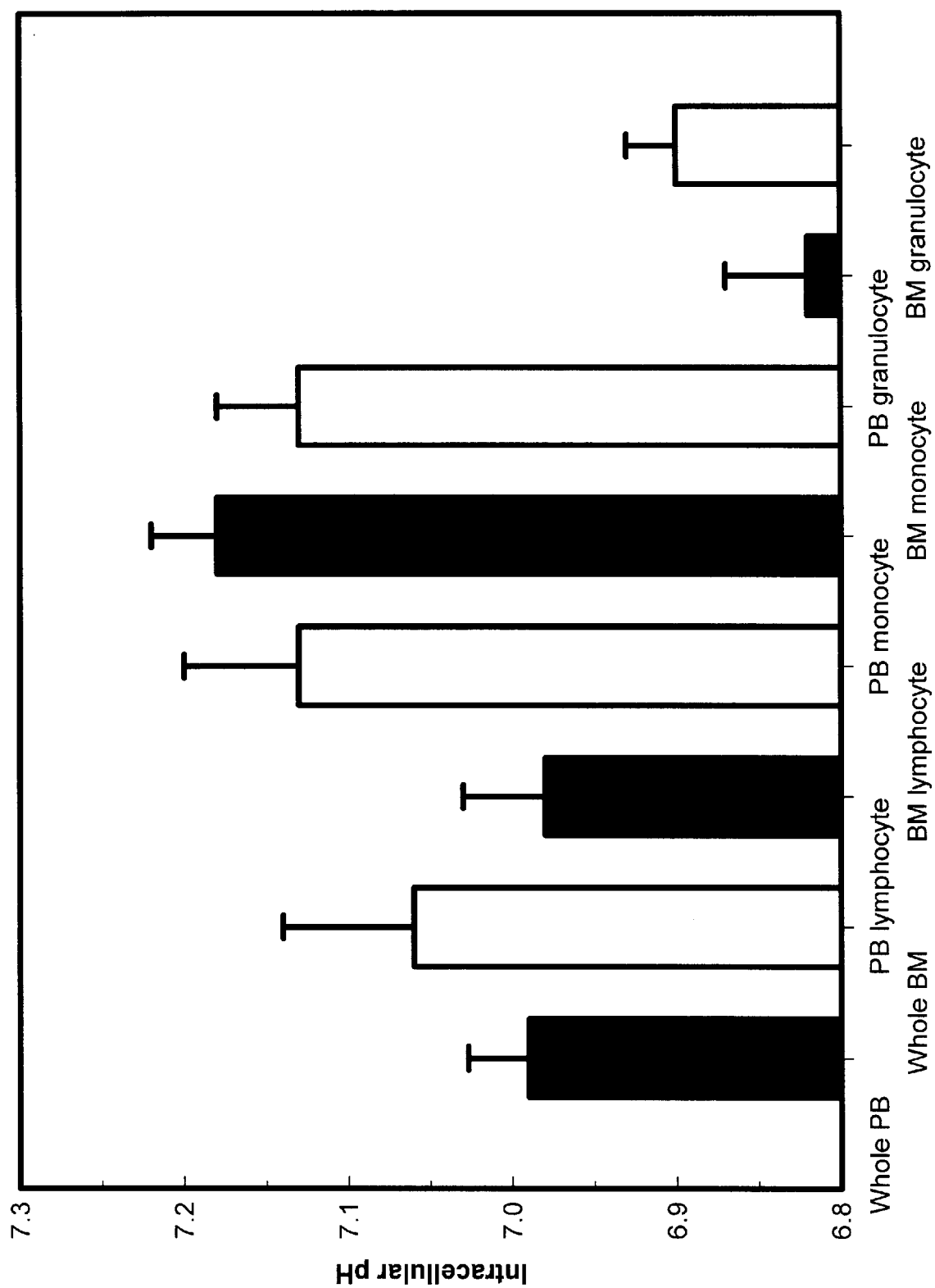
FIG. 1 shows intracellular pH of normal peripheral blood and bone marrow measured by flow cytometry.

Using flow cytometry and the pH-sensitive fluorescent indicator, SNARF, we first determined the pH$_i$ of normal human peripheral blood (PB) and bone marrow (BM) mononuclear cells. FIG. 1 shows that no significant difference (p>0.05) in pH$_i$ occurred between PB (pH$_i$=6.99±0.037, n=25) and BM (pH$_i$=7.06±0.08, n=10). Also shown in FIG. 1 are pH$_i$ values for the lymphocyte, monocyte and granulocyte flow cytometric gates for normal PB and BM, indicating that different haemopoietic subpopulations exhibit different pH$_i$ values (manuscript in preparation). For the present discussion, all pH$_i$ values are given for the whole sample rather than individual subpopulations.

Figure 2:
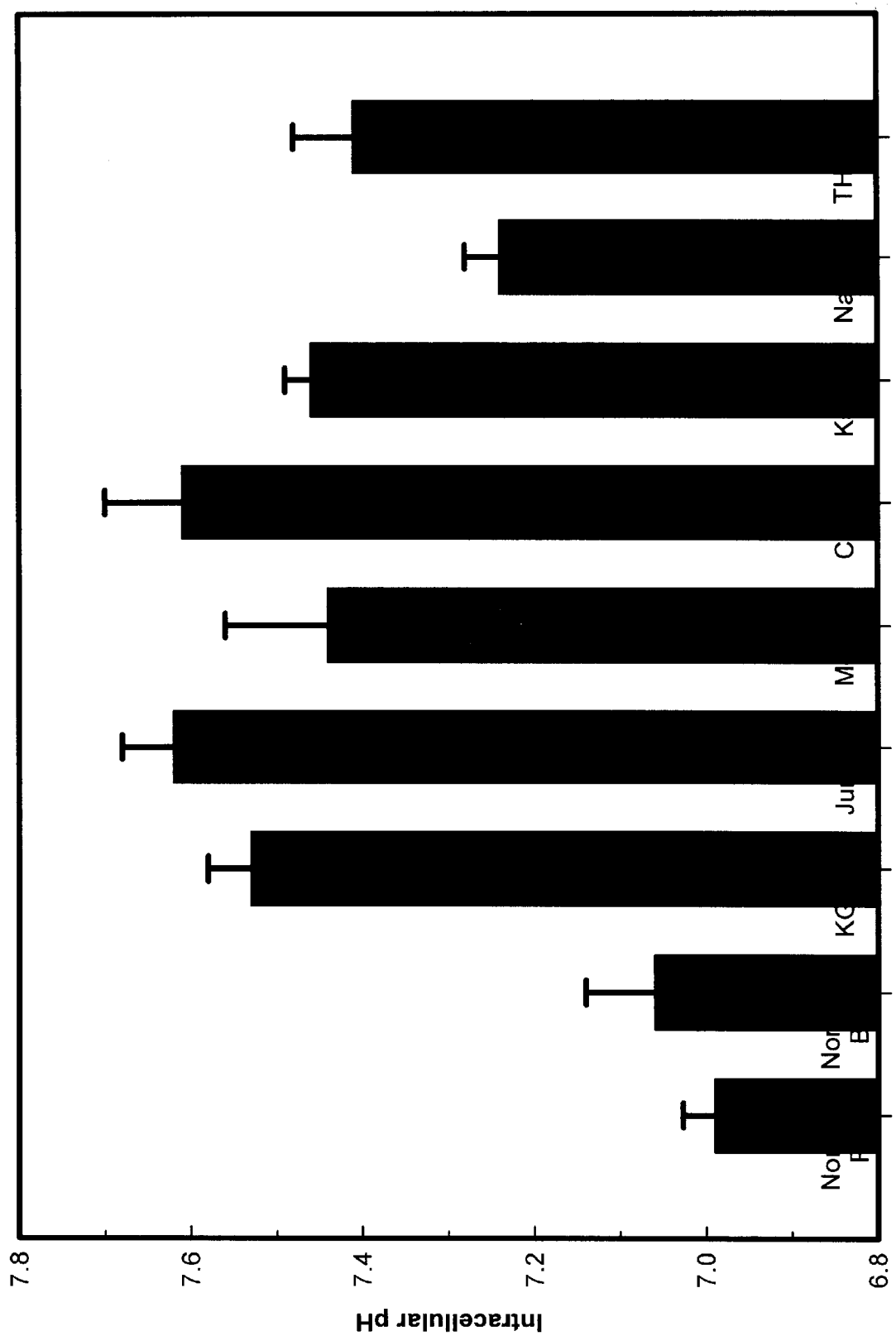
FIG. 2 shows a comparison of pH$_i$ values from normal peripheral blood and bone marrow (FIG. 1) with those from 7 different human leukemic cell lines.

Having obtained baseline pH$_i$ values for normal cells, we then demonstrated that various different leukaemic cell lines exhibit a higher pH$_i$ (p<0.01) than normal PB and BM (FIG. 2). These observations were concordant with those of previous reports describing intracellular alkalinisation of continuously proliferating cell lines, but prompted review of the behavior of primary leukaemic samples.

Figure 3:
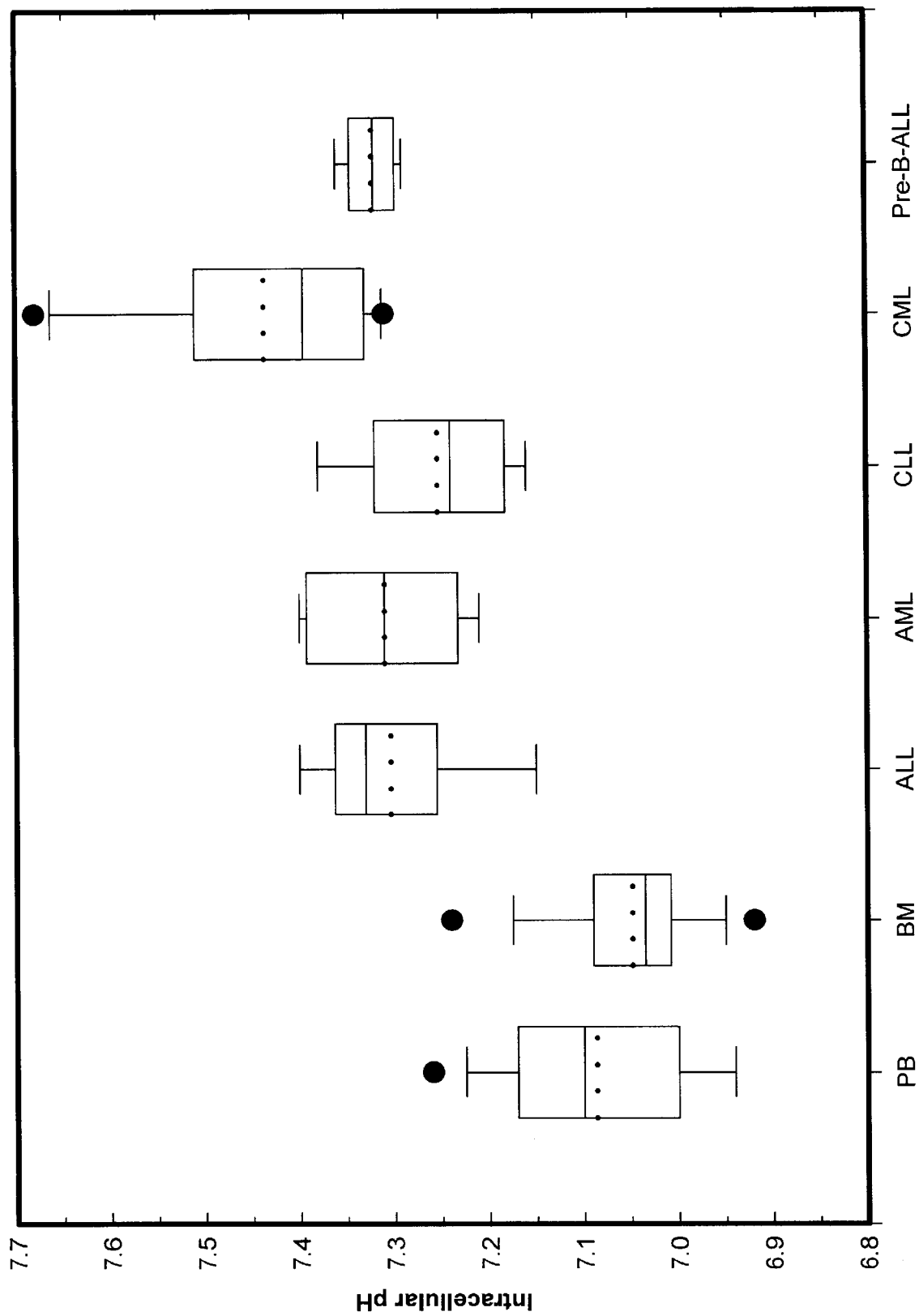
FIG. 3 illustrates box and whisker plots for normal peripheral blood and bone marrow (FIG. 1) and primary leukemic patient samples.

FIG. 3 shows the pH$_i$ values of samples obtained from patients with different leukaemias. The box and whisker plots showing all the relevant statistical information are described in the legend. In addition, a statistically higher pH$_i$ of ALL (p=0.005), AML (p=0.004), CLL (p=0.049), CML (p<0.001), and pre-B-ALL (p=0.002) peripheral blood samples compared to normal donors could be demonstrated using analysis of variance. Thus, primary leukaemic cells exhibit a higher pH$_i$ than normal, in a manner comparable to cell lines. This would imply a correlation between the state of activity of the NHE-1 and cellular proliferative status.

Figure 4:
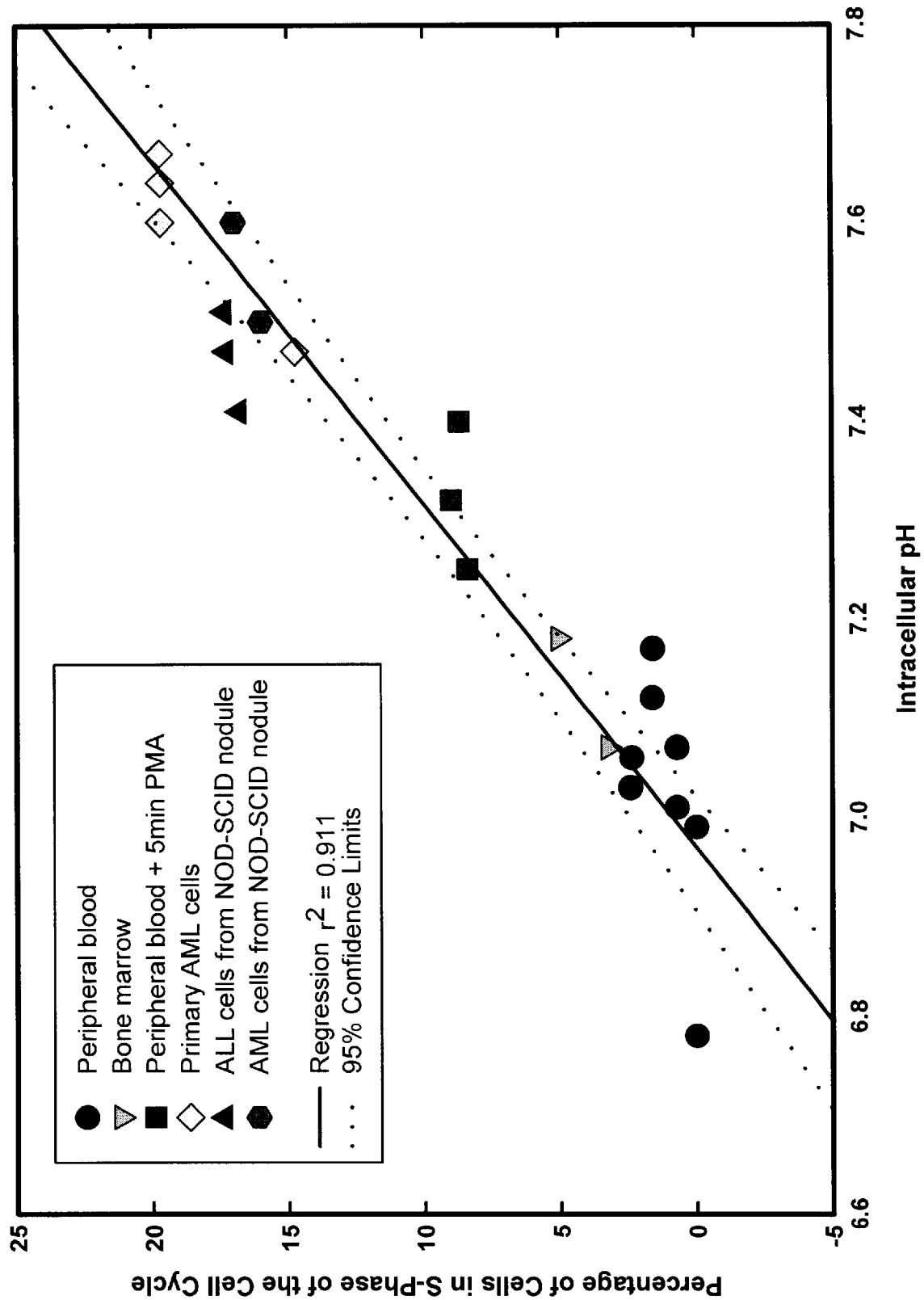
FIG. 4 shows a correlation between pH$_i$ and cell cycle.

The pH$_i$ and the percentage of cells in S-phase of the cell cycle were simultaneously determined in aliquots of the same sample, using propidium iodide labeling. Prior to analysis, peripheral blood was also incubated with phorbol ester to activate the NHE-1. Samples incubated with phorbol ester showed a statistically higher (p=0.003) pH$_i$ (7.32±0.043) than unstimulated PB (7.03±0.04) and showed a statistically greater (p<0.001) proportion of cells in S-phase (8.7%±0.17%) than untreated PB (1.19%±0.34%). Furthermore, there was a direct correlation between pH$_i$ and proportion of cells in S-phase in both normal and neoplastic haemopoietic cells of various origins (FIG. 4). Thus, intracellular alkalinisation is associated with an increased proliferation and possibly transformation of haemopoietic cells. We hypothesized that unregulated proliferation of leukaemic cells might, at least in part, be due to suppression of normal apoptotic mechanisms. In this case, inhibitors of the NHE-1 would be expected to induce apoptosis in leukaemic cells, and we therefore examined the effects of NHE-1 inhibitors upon such cells.

Figure 5A:
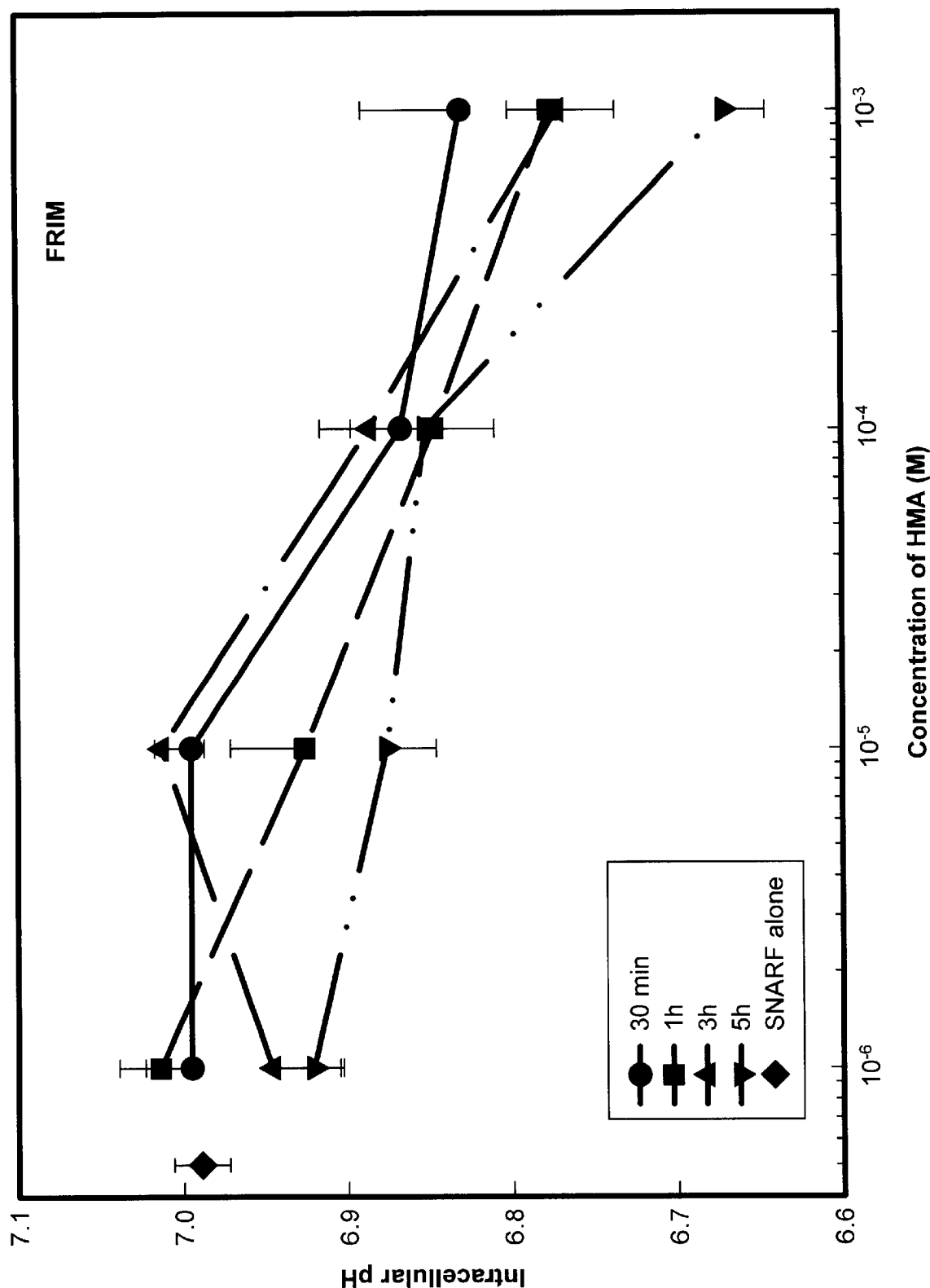
FIGS. 5A–5D illustrate the effect of HMA on the pH$_i$ and apoptosis of normal peripheral blood cells.
Figure 5B:
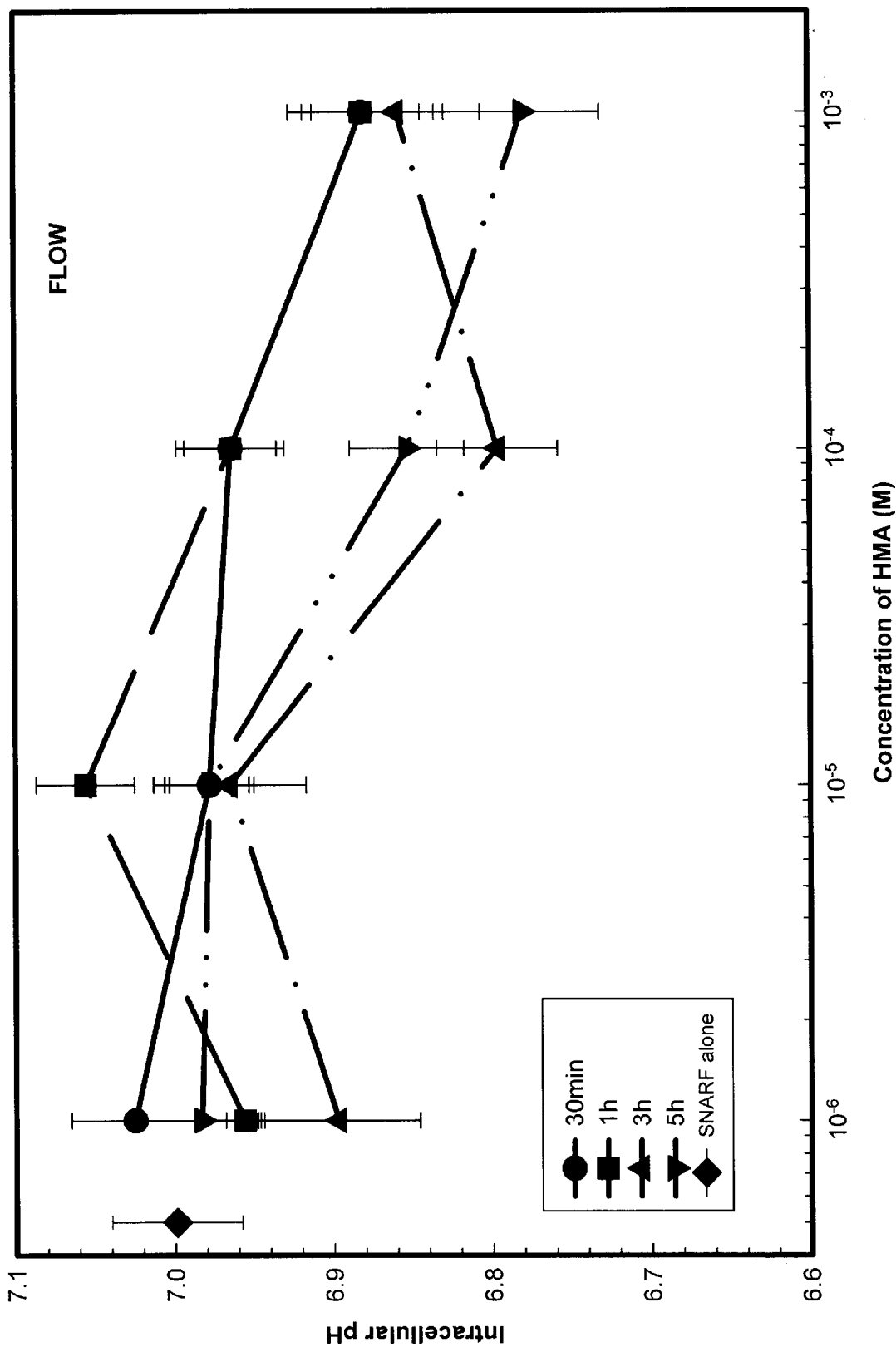
Figure 5C:
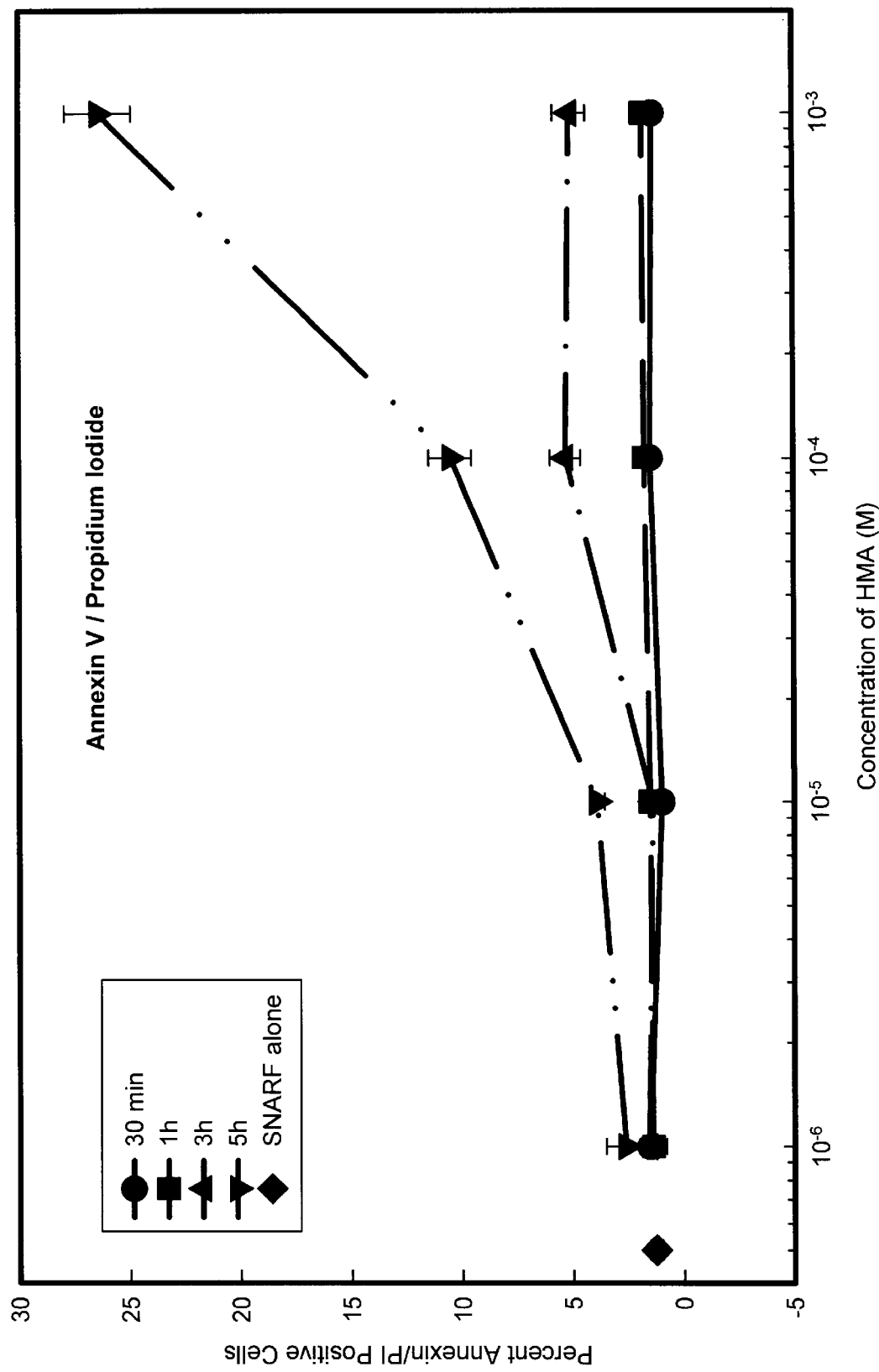
Figure 5D:
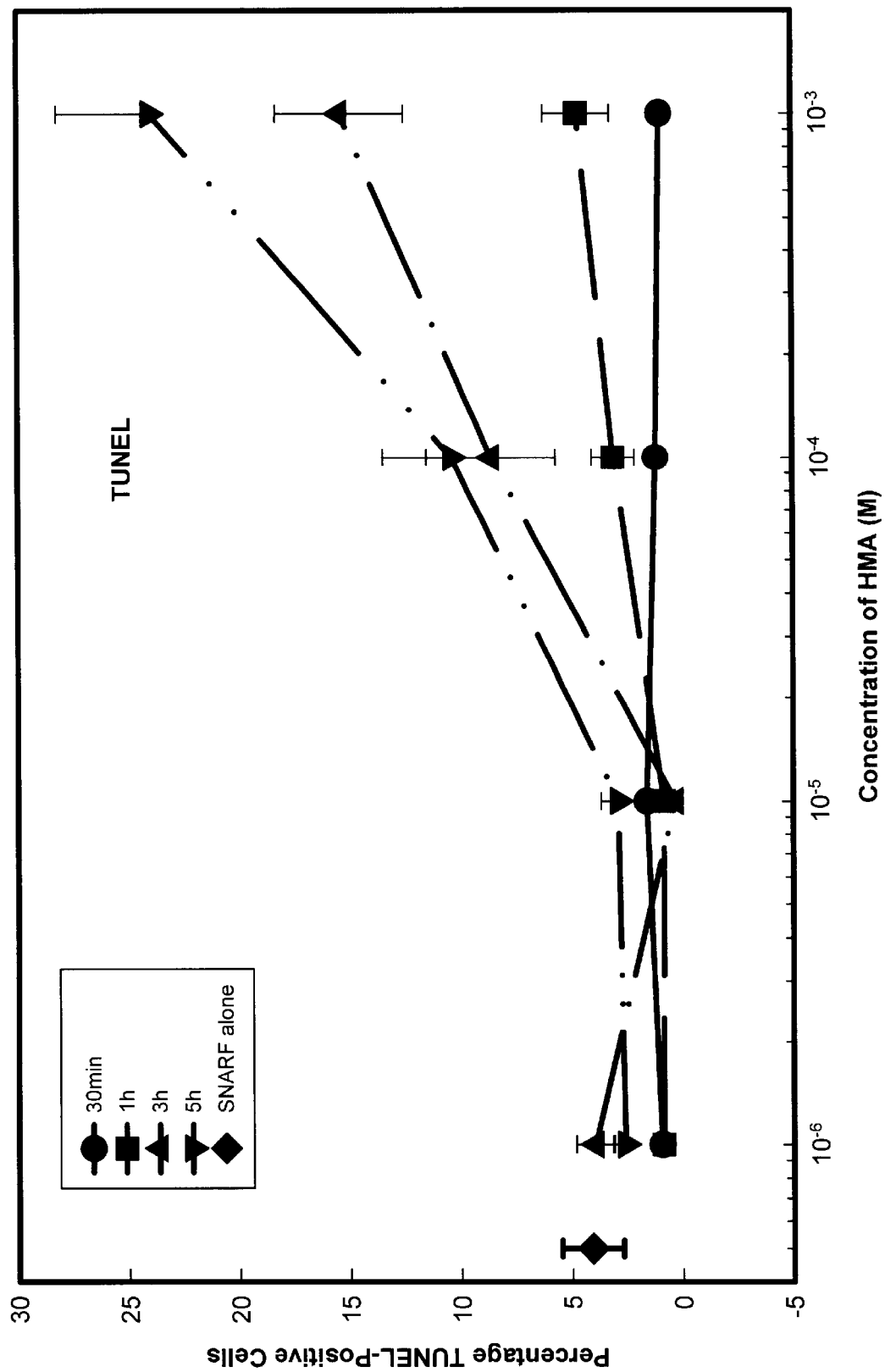

Normal peripheral blood cells were incubated in the absence or presence of the NHE-1 inhibitor, 5-(N,N-hexamethylene)-amiloride (HMA), at concentrations ranging from $10^{-7}$M to $10^{-4}$M for up to 5h. Cells were then aliquoted so that $pH_i$ and apoptotic measurements could be performed. In these experiments, $pH_i$ was measured using both flow cytometry and fluorescence ratio imaging microscopy (FRIM). FIGS. 5A and 5B show that the greatest inhibition occurred at 5h, using the highest HMA concentration ($10^{-4}$M). Likewise, the greatest proportion of apoptotic cells was found after 5h incubation with $10^{-4}$M HMA (FIGS. 5C and 5D), using both annexin-V and TUNEL techniques. The proportion of necrotic cells measured by propidium iodide (PI) remained constant at about 5% in the absence or presence of HMA for each time point measured. Flow cytometric profiles showed that the proportion of annexin-V/PI-positive cells (FIG. 5C) was due to increasing numbers of cells first becoming annexin-V positive (data not shown) and then double-positive for both dyes. It is interesting to note that both methods measured about 25% apoptotic cells when $pH_i$ was reduced to about 6.8. As shown in the next section, a $pH_i$ of 6.8 appears to be a critical value below which increased apoptosis occurs.

Leukaemic cell lines (KG-1a and CEM) were incubated for varying periods of time with $10^{-4}$M HMA and $pH_i$ and apoptosis measured. For both cell lines, in the absence of HMA, $pH_i$ ranged from 7.43±0.1 at time zero to 6.9±0.08 after 5h of incubation. However, after 5h with HMA, the $pH_i$ had decreased to 5.6±0.07 (n=4) for KG-1a and 6.1±0.06 (n=4) for CEM cells. In the absence of HMA, the percentage of KG-1a and CEM cells undergoing apoptosis, measured by annexin-V, ranged from 2% to 9% for the duration of the experiment, whereas by 5h in the presence of HMA, the percentage of KG-1a or CEM cells undergoing apoptosis ranged from 70–80%. In addition, denaturing RNA gel electrophoresis demonstrated that RNA from KG-1a cells treated with $10^{-4}$M HMA began to degrade between 30 min and 1h after addition, and that total degradation had occurred by 3h (data not shown).

Figure 6A:
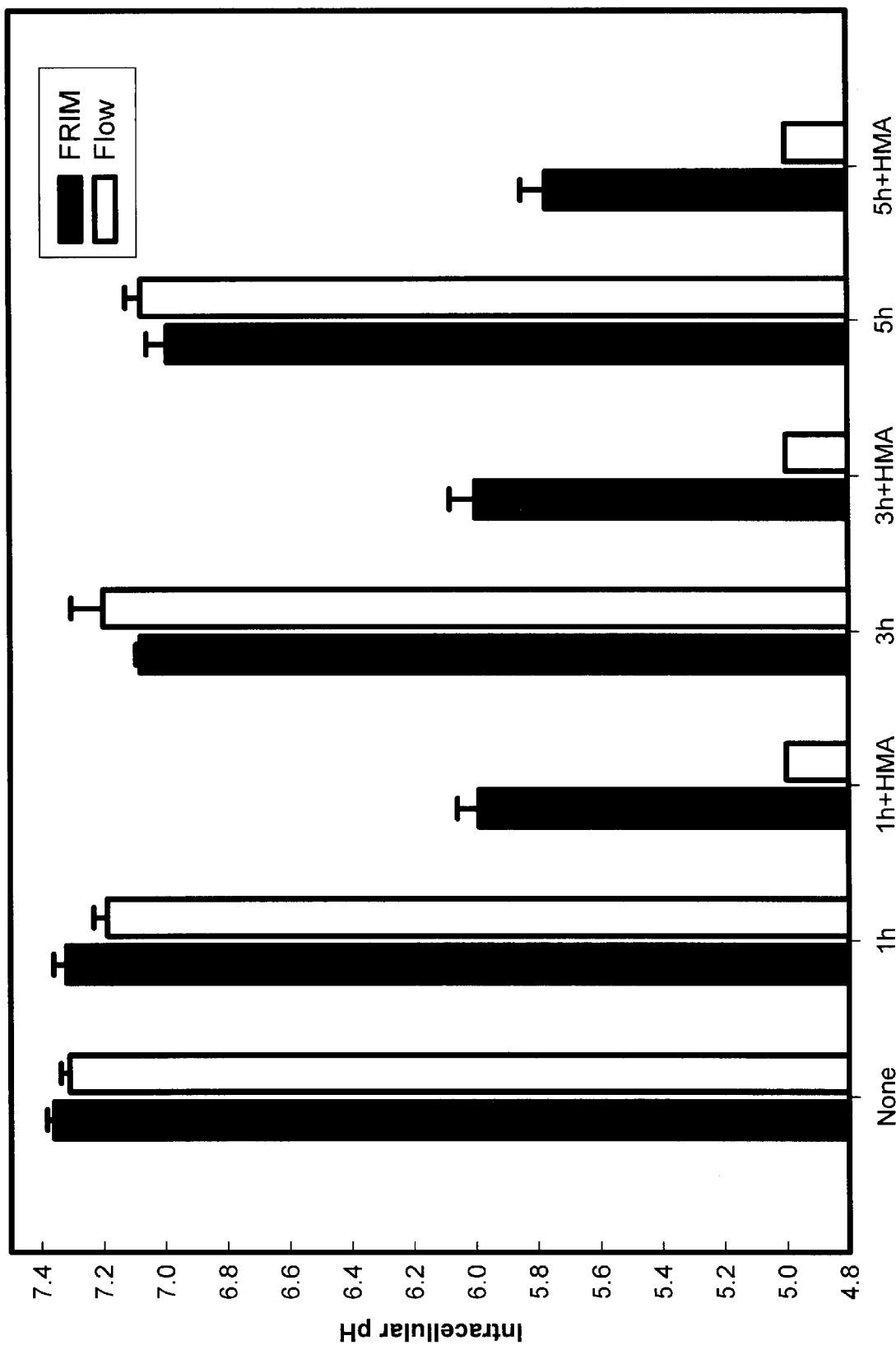
FIGS. 6A and 6B show the effect of HMA on pH$_i$ and apoptosis of primary acute lymphoblastic leukemic cells.
Figure 6B:
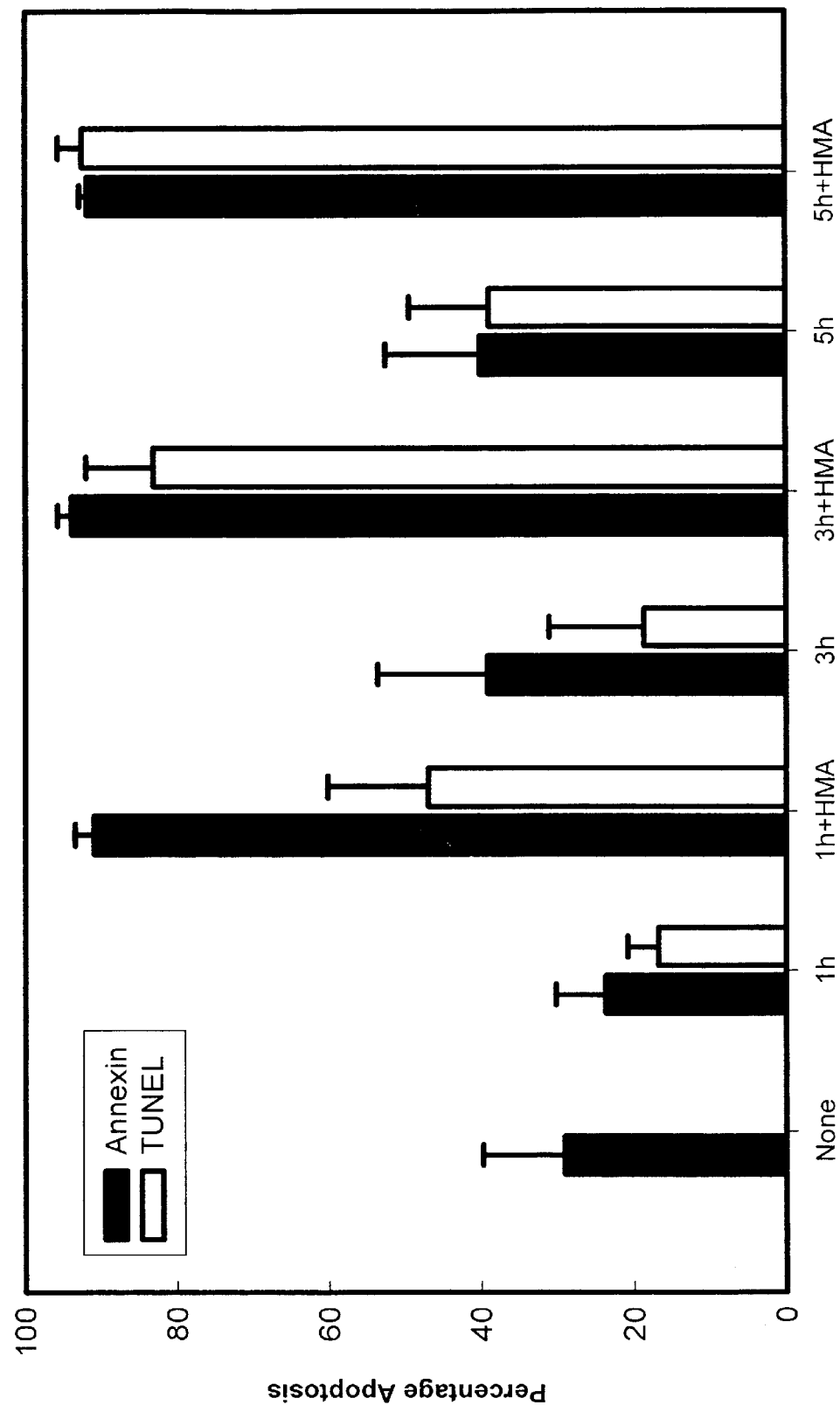

FIG. 6A shows the effect on $pH_i$ and FIG. 6B shows the percentage of apoptosis of incubating fresh ALL patient leukaemic cells with $10^{-4}$M HMA for up to 5h. Intracellular pH was measured by both FRIM and flow cytometry, while apoptosis was measured by annexin-V and TUNEL. In the presence of pharmacological doses of HMA, $pH_i$ was rapidly reduced compared with cells incubated in the absence of HMA. In fact, in all experiments, $pH_i$ of the cells measured by flow cytometry was too low to calibrate. For this reason, $pH_i$ values for 1h, 3h and 5h were set at 5.0. After 1h, the proportion of cells incubated with HMA undergoing apoptosis was about 85% using annexin-V and about 60% using the TUNEL technique. After 5h incubation, both methods indicated that over 90% of the cells were apoptotic. Thus, primary ALL cells showed greater sensitivity to HMA than normal PB, thereby demonstrating an important differential effect between normal and acute lymphoblastic leukaemic cells.

Normal murine bone marrow cells can be stimulated by interaction of extracellular matrix proteins with the $\alpha_4$-integrin subunit, leading to activation of the $Na^+/H^+$ exchanger, an increase in $pH_i$ and proliferation of hemopoietic stem and progenitor colony-forming cells in the absence of growth factors (8). From these studies, it was hypothesized that continuously proliferating cells would exhibit a constitutively higher $pH_i$ than normal cells due to sustained activation of the $Na^+/H^+$ exchanger, with a concomitant suppression of apoptosis.

The results presented here demonstrate that primary leukemic cells indeed exhibit a greater $pH_i$ than normal hemopoietic cells, allowing $pH_i$ measurements to be used as a biomarker for leukemic cells. Furthermore, direct correlation between $pH_i$ and the proportion of cells in S-phase could allow detection of abnormal proliferating cell populations by measurement of $pH_i$. This correlation has an additional implication, namely that a sustained increase in $pH_i$ may be one of the mechanisms driving or facilitating neoplastic transformation and/or proliferation (12). Since expression and activity of the $Na^+/H^+$ exchanger has been shown to be required for tumor growth (12, 13), it follows that methods to decrease $pH_i$ may have potential in the therapy of neoplasms. This possibility prompted us to study the effects of an NHE-1 inhibitor on $pH_i$ and apoptosis of leukemic cells. The results clearly show that the amiloride analogue, HMA, can induce apoptosis within 1 h in primary leukemic cells and that more than 90% of the cells are either dead or undergoing apoptosis between 3 and 5 h of incubation. These results are concordant with several reports in which reduced $pH_i$ of hemopoietic cells increased levels of apoptosis (9–11). In 1992, Harguindey and Cragoe (14) suggested that amiloride analogues could be used to control metastasis and cancer multidrug resistance. Horvat et al (15) and Hasuda et al (16) demonstrated that following acidification of the extracellular milieu using the ionophore nigericin, addition of amiloride analogues, notably 5-(N-ethyl-N-isopropyl) amiloride (EIPA), were able to mediate an anti-tumor. When combined with amiloride analogues, both hypoxia (17) and hyperthermia (18), which reduce the extracellular pH, exhibited an anti-tumor effect. Although the amiloride analogues HMA and EIPA, demonstrate greater potency and specificity of NHE-1 inhibition than amiloride itself (19), the mechanism of apoptotic induction observed in the current study is unknown and is being investigated at present. Nevertheless, we have demonstrated for the first time a clear correlation between modulation of $pH_i$ and an increased number of cells in S-phase on the one hand and apoptosis on the other.

Although we would expect normal cells to be affected by treatment with HMA, a differential sensitivity and the pro-apoptotic effects of HMA on leukaemic cells were demonstrated. This study therefore lays the groundwork for exploration of the novel and potential anti-leukaemic properties of NHE-1 inhibitors in vivo.

Normal peripheral blood (PB) and bone marrow (BM) mononuclear cell samples were obtained from adult donors after approved Institutional Research Board (IRB) consent forms had been signed. Similarly, samples from leukaemic patients were also obtained after consent had been given.

The following human leukemic cell lines were originally obtained from ATCC (Rockville, Md.): KG-1a (BM acute myelogenous leukemia), Jurkat (acute T-cell leukemia), Molt-4 (PB acute lymphoblastic leukemia), CEM (PB acute lymphoblastic leukemia), K562 (chronic myeloid leukemia), THP-1 (acute monocytic leukemia), Nalm-6 (B-cell leukemia). All cell lines were cultured in Dulbecco's Modified Eagles Medium (DMEM) containing 10% heat-inactivated fetal bovine serum (FBS). Only cells in log phase growth were used.

In experiments involving both $pH_i$ and cell cycle measurements (see below), primary patient leukemic samples were grown and expanded in non-obese diabetic, severe combined immunodeficient (NOD-SCID) mice. This involved subcutaneous injection of $1\times10^7$ cells suspended in 100 µl of MATIGEL™ (Becton Dickinson, San Jose, Calif.) into untreated NOD-SCID mice as described previously by Yan et al. (20). After 4–8 weeks, palpable subcutaneous nodules were excised. A single cell suspension was prepared after collagenase/dispase digestion for 45 min at 37 C and repeated pipetting. Cells isolated from such nodules were found to be phenotypically and cytogenetically identical to those cells used for the primary inoculation.

Normal PB cells were incubated for 5 min with $10^{-6}$ M phorbol-12-myristate-13-acetate (PMA, Sigma Chemical Company, St. Louis, Mo.) to non-specifically activate the NHE-1. Thereafter the cells were washed with phosphate buffered saline (PBS).

Measurement of $pH_i$ for hemopoietic cells has been described in detail elsewhere (8). Briefly, intracellular pH was measured by both flow cytometry and FRIM by incubating cells with carboxy SemiNaphthoRhodaFluor-1 acetoxymethyl ester, acetate (carboxy SNARF-1 AM, Molecular Probes, Eugene, Oreg.) for 15 min at room temperature. SNARF is excited at 488 nm and emits at 580 nm and 640 nm. The ratio of the emission wavelengths 640/580 was used (8) to estimate the $pH_i$ from a calibration curve. The calibration curve was performed using the nigericin clamp technique (21). After SNARF labeling, aliquots of cell suspension were resuspended in a high $K^+$-containing buffer at a specific pH (usually 6.8, 7.0, 7.2, 7.4, 7.6 for flow cytometry and 7.8 or 6.6, 7.0, 7.4 and 7.8 for FRIM). The cell suspensions were then clamped at the specific pH value, by addition of 0.03 µM nigericin (Molecular Probes). Nigericin is an ionophore which allows exchange of $H^+$ for $K^+$ ions by abolishing the pH gradient across the cell membrane. Thus, when the internal and external $K^+$ concentrations are approximately the same, the pH rapidly equilibrates to the pH of the bathing solution. For flow cytometry, 50,000 events were acquired either on a FACSort™ flow cytometer (Becton-Dickenson). Using FRIM, microscopic images were acquired using two image intensifying charged couple digital (ICCD) cameras (for 580 nm and 640 nm) attached to a Zeiss Axiovert 150 microscope. Attofluor Ratio Vision software was used to acquire and analyze the data. Flow cytometric results were analyzed using WinList Software (Verity Software House Inc. Topsham, ME) to obtain fluorescence ratio measurements. For both flow cytometry and FRIM analysis, the calibration curves were obtained and sample $pH_i$ values determined from the fluorescence ratio values using Table Curve software (SPSS Inc., Chicago, Ill.).

The proportion of cells in S-phase of the cell cycle was determined using the propidium iodide technique using the CycleTEST Plus DNA reagent kit (Becton-Dickinson, San Jose, Calif.). Data were acquired by flow cytometry, and analyzed using the Modfit LT software program (Verity Software House Inc).

Two methods were used to determine if reduction in $pH_i$ induced apoptosis. The first used annexin-V conjugated to fluorescein isothiocyanate (FITC) (Pharmingen, San Diego, Calif.) to determine the translocation of phosphatidylserine from the inside to the outside of the plasma membrane. Cells were counter-stained with propidium iodide (PI) to determine the proportion of necrotic cells. Cell staining was performed according to the manufacturer's instructions. The second technique used terminal deoxynucleotidyl transferase (TdT)-mediated dUTP nick-end labeling (TUNEL) of fragmented DNA. Fluorochrome (FITC)-labelling of DNA (Boehringer Mannhein, Germany) was performed according to the manufacturer's instructions and measurements performed by flow cytometry.

The amiloride analogue, HMA (Sigma Chemicals, St. Louis, Mo.) was dissolved in dimethylsulphoxide (DMSO) and a stock solution ($10^{-3}$M) prepared in DMEM. Cells were incubated at concentrations ranging from $10^{-7}$M to $10^{-4}$M for varying periods of time specified in the results. After incubation, cells were washed and aliquoted according to the type of measurement ($pH_i$ or apoptosis) performed. Controls included cells not treated with HMA.

The number (n) of experiments performed is given in each legend. All results are given as the mean±standard error of the mean (SEM) for the given number of experiments stated in the legends. Statistical significance was determined either using the two-way, unpaired t-test or one-way analysis of variance.

It will be apparent to those skilled in cellular biology and cancer treatment that many modification and substitutions can be made to the just-described preferred embodiments without departing from the spirit and scope of the present invention.

EXAMPLE 1

The procedure of the present invention is capable of producing simultaneously, all the information required to determine and potentially separate a proliferating cell population from a non-proliferating cell population. Furthermore, it can be used to simultaneously accrue information on whether the intracellular pH of a specific population has been decreased by the administration of a drug which either inhibits the sodium/hydrogen exchanger or generally reduces the intracellular pH, thereby inducing apoptotic cell death. The general procedure is as follows:

Step 1. Peripheral blood or bone marrow is obtained in the presence of an anti-coagulating agent, e.g. heparin. Red blood cells and plasma are separated from the remaining cells, which are termed "mononuclear cells" or MNCs. This can be performed using commercially available cell separation reagents.

Step 2. After washing the mononuclear cells by suspending them into medium or phosphate buffered saline (PBS), centrifuging the cells at 200×g for 10 minutes into a pellet at the bottom of a tube and removing the liquid, the cells are again resuspended in a small amount PBS and the cell concentration determined using an automatic cell counter. Approximately 1 million ($1\times10^6$) cells are generally required for each sample. However, to evaluate the $pH_i$ of the sample population, a calibration curve has to be obtained. This involves setting the $pH_i$ of 6 similar cells suspensions so that a range from pH 6.8 to 7.8 in 0.2 pH unit divisions can be performed. This covers the normal $pH_i$ range. Therefore, for a single $pH_i$ determination, the cell suspension has to be divided into at least 7 aliquots or portions each with the same cell concentration present. Furthermore, since the addition of fluorescent labeled antibodies can result in background fluorescence, three extra control tubes containing cells are required.

Step 3. Labeling with fluorescent antibody in order to define a cell population: The cells in all but three of the tubes are now labeled with antibody to which a fluorescent label has been chemically bound. Such antibodies are commercially available. One antibody is labeled with a fluorescent dye called fluorescene isothiocyanate (FITC). The other is labeled with a fluorescent dye called allophycocyanin (APC). Labeling occurs by incubating the cells with the fluorescent bound antibody for about 20–30 min on ice (4° C.), followed by washing the cells as described in Step 2 to remove the remaining label. The antibodies bind to different membrane antigens on the surface and are used to define a specific population.

One of the three tubes of cells that were not labeled in this way remains as an unlabeled control. The other two tubes are labeled with control antibodies to which the same fluorescent dye is bound. Control antibodies are called isotype controls. These isotype controls are the same antibody type as those used for the sample, but are not directed to any specific membrane antigens. They are used for detecting non-specific binding of the antibody to the cell.

Step 4. Labeling with a pH-sensitive fluorescent dye and preparation of the pH calibration curve. To the cells that have been labeled with antibodies, the pH sensitive fluorescent dye is now added. For this procedure, carboxy Semi-NaphthoRhodaFluor (SNARF)-1, acetoxymethyl ester, acetate (carboxy SNARF-1 AM) is used. The cells are incubated with a final concentration of 10 $\mu$M (micro molar) SNARF-1 for 20–30 min. at room temperature. No serum of any kind must be present at this step, and if present beforehand, must be removed by washing the cells. The cells used for calibration are also treated in the same manner. After the incubation time has elapsed, the cells are washed in PBS.

The tubes containing the cells to be used for the calibration must now be further treated. For this, buffers containing a high potassium concentration and set at pH values of 6.8, 7.0, 7.2, 7.4, 7.6, and 7.8 are prepared. To each of the tubes containing the cells for calibration, one of the buffers set at a specific pH is added and the cells resuspended. To each tube, a final concentration of 2 $\mu$M/ml nigericin is added. (Nigericin allows exchange of hydrogen ions for potassium ions so that when the internal and external potassium concentrations are the same, the intracellular pH rapidly equilibrates to the pH of the bathing solution).

Step 5. Labeling with Hoechst 33342 to assess the cell cycle status of the population. For the sample only, the cells are now incubated with 1 $\mu$M/ml of Hoechst 33342 (Molecular Probes, Eugene, Oreg.) for 20 min at room temperature in the dark. Thereafter, the cells are briefly washed and analysis can be performed.

Step 6. Measurements required. The measurements have to be performed on a flow cytometer. Separation of cells using this procedure has to be performed on a flow cytometer capable of cell sorting. This type of equipment is then known as a fluorescent activated cell sorter (FACS™). The flow cytometer or FACS™ has to equipped for measuring fluorescence intensity at different wavelengths. The excitation and emission wavelengths for each of the fluorescent dyes used in this procedure are as follows:

Table of Fluorochromes used in the Procedure

| Fluorochrome | Excitation (nm) | Emission (nm) | Wavelength color | Laser type required |
|---|---|---|---|---|
| FITC | 495 | 519 | Green | Argon |
| APC | 650 | 660 | Red | Helium-neon |
| SNARF-1 | 548 | 587 | Yellow | Argon |
| SNARF-1 | 579 | 635 | Orange to Red | Argon |
| Hoechst 33342 | 345 | 478 | UV (blue) | UV |

The table shows that three different laser types are required to perform this procedure. Furthermore the equipment software used must be capable of analyzing the fluorescence intensity produced by SNARF-1 as a fluorescence ratio (540/640 nm) on-line. This method of analysis is called the "ratiometric method". Hoechst 33342 is used in this method for two reasons. First Hoechst 33342 emits in the UV wavelength region so that it does not overlap with the other fluorochromes used. (Other fluorochromes can be used for cell cycle analysis, but would not allow measurement of intracellular pH because they would their wavelengths would overlap with those of SNARF-1). Second, for the analysis of cell cycle on-line, it is only necessary to know whether the intensity emitted from the dye is "dim" or "bright". When cells are quiescent (in $G_0$ of the cell cycle), Hoechst 33342 is not taken up by the cells and not actively pumped out of the cells. When cells are in cell cycle, the dye is rapidly taken up by the cells, but also actively pumped out of the cells.

Step 7. Data acquisition and cell separation. Data is acquired on the controls and sample in order to "set" the machine for sorting. To sort the cells into proliferating and non-proliferating cells, the FACS has to be calibrated and "gates" set so that the population to be sorted has the following characteristics:

Proliferating cells: high $pH_i$ ($pH_i$>7.15), Hoechst $33342^{bright}$

Non-proliferating cells: low $pH_i$ ($pH_i$<7.15), Hoechst $33342^{dim}$

Since, the $pH_i$ and the proportion of cells in S-phase of the cell cycle are directly correlated with each other, using both high $pH_i$ and Hoechst $33342^{bright}$ parameters to sort proliferating cells increases the likelihood of obtaining the required cell population.

LITERATURE CITED

The following publications are incorporated by reference as if fully set out herein.

1 Fliegel, L. & Frohlich, O. The $Na^+/H^+$ exchanger: an update on structure, regulation and cardiac physiology. *Biochem J* 296, 273–285 (1993).

2 Wakabayashi, S., Shigekawa, M., & Pouyssegur, J. Molecular physiology of vertebrate $Na^+/H^+$ exchangers. *Physiol.Rev.* 77, 51–74 (1997).

3 Lifton, R. P., Sardet, C., Pouyssegur, J., & Lalouel, J. M. Cloning of the human genomic amiloride-sensitive $Na^+/H^+$ antiporter gene, identification of genetic polymorphisms, and localization on the genetic map of chromosome 1p. *Genomics* 7, 131–135 (1990).

4 Whetton, A. D. et al. Interleukin-3-stimulated haemopoietic stem cell proliferation. Evidence for activation of protein kinase C and $Na^+/H^+$ exchange without inositol lipid hydrolysis. *Biochem.J.* 256, 585–592 (1988).

5 Vallance, S. J., Downes, C. P., Cragoe, E. J., & Whetton, A. D. Granulocyte-macrophage colony-stimulating factor can stimulate macrophage proliferation via persistent activation of $Na^+/H^+$ antiport. Evidence for two distinct roles for $Na^+/H^+$ antiport activation. Biochem.J. 265, 359–364 (1990).

6 Li, J. & Eastman, A. Apoptosis in an interleukin-2-dependent cytotoxic T lymphocyte cell line is associated with intracellular acidification. Role of the Na(+)/H(+)-antiport. J *BiolChem* 270, 3203–3211 (1995).

7 Rebollo, A. et al. Apoptosis induced by IL-2 withdrawal is associated with an intracellular acidification. *Exp Cell Res* 218, 581–585 (1995).

8 Rich, I. N., Brackmann, I., Worthington-White, D., & Dewey, M. J. Activation of the sodium/hydrogen exchanger via the fibronectin-integrin pathway results in hematopoietic stimulation. *J. Cell.Physiol.* 177, 109–122 (1998).

9 Perez-Sala, D., Collado-Escobar, D., & Mollinedo, F. Intracellular alkalinization suppresses lovastatin-induced apoptosis in HL-60 cells through the inactivation of the pH-dependent endonuclease. *J Biol Chem* 270, 6235–6242 (1995).

10 Chen, Q. et al. Role of acid/base homestasis in the suppression of apoptosis in haemopoietic cells by v-Abl protein tyrosine kinase. *J Cell Sci* 110, 379–387 (1997).

11 Tsao, N. & Lei, H. Y. Activation of the Na(+)/H(+) antiporter, Na+/HCO3(−)/CO3(2−) cotransporter, or Cl(−)/HCO3(−) exchanger in spontaneous thymocyte apoptosis. *J Immunol* 157, 1107–1116 (1996).

12 Rotin, D., Steele-Norwood, D., Grinstein, S., & Tannock, I. Requirement of the $Na^+/H^+$ exchanger for tumor growth. *Cancer Res* 49, 205–211 (1989).

13 Pouyssegur, J., Sardet, C., Franchi, A., L'Allemain, G., & Paris, S. A specific mutation abolishing $Na^+/H^+$ antiport activity in hamster fibroblasts precludes growth at neutral and acidic pH. *Proc.Natl.Acad.Sci. U.S.A.* 81, 4833–4837 (1984).

14 Harguindey, S. & Cragoe EJ, J.r. the $Na^+/H^+$ antiporter in oncology in the light of the spontaneous regression of cancer and cell metabolism. *Med Hypotheses* 39, 229–237 (1992).

15 Horvat, B., Taheri, S., & Salihagic, A. Tumor cell proliferation is abolished by inhibitors of $Na^+/H^+$ and $HCO3^-/Cl^-$ exchange. *Eur.J.Cancer* 1992. 29A, 132–137 (1997).

16 Hasuda, K., Lee, C., & Tannock, I. F. Antitumor activity of nigericin and 5-(N-ethyl-N-isopropyl)amiloride: an approach to therapy based on cellular acidification and the inhibition of regulation of intracellular pH. *Oncol.Res* 6, 259–268 (1994).

17 Tannock, I. F. & Rotin, D. Acid pH in tumors and its potential for therapeutic exploitation.Cancer Res. Aug. 15. 1989. 49, 4373–4384 (1997).

18 Liu, F. F., Diep, K., & Hill, R. P. The relationship between thermosensitivity and intracellular pH in cells deficient in Na+/H+ antiport function. *Radiother Oncol* 40, 75–83 (1996).

19 Kleyman TR & Cragoe EJ. Amiloride and its analogs as tools in the study of ion transport. *J Membrane Biol* 105, 1–21 (1988).

20 Yan, Y. et al. Growth pattern and clinical correlation of subcutaneously inoculated human primary acurte leukemias in severe combined immunodeficiency mice. *Blood* 88, 3137–3146 (1996).

21 Thomas JA, Buchsbaum RN, Zimniak A, & Racker E. Intracellular pH measurements in Ehrlich ascites tumor cells utilizing spectroscopic probes generated in situ. *Biochemistry* 18, 2210–2218 (1979).

What is claimed is:

1. A method of inhibiting cellular proliferation by reducing the internal pH of a cell, comprising the steps of:

(a) harvesting cells from a human or animal;
    (b) labeling the cells with a fluorescent marker antibody capable of selectively identifying a cellular membrane marker;
    (c) labeling the cells with a pH-sensitive fluorescent dye;
    (d) labeling the cells with a fluorescent cell cycle marker;
    (e) applying the cells to a flow cytometry cell sorter and analyzing the cells for the fluorescent intensities of the marker antibody, the cell cycle marker, and the pH-sensitive dye;
    (f) sorting the analyzed cells into a low internal pH population and a high internal pH population;
    (g) inducing apoptosis in the sorted cell population having a high internal pH by adding a $Na^+/H^+$ exchanger inhibitor, and thereby inhibiting cellular proliferation.

2. The method of claim 1, wherein the harvested cells are human or animal peripheral blood cells or bone marrow mononuclear cells.

3. The method of claim 1, wherein the harvested cells are leukemic cells.

4. The method of claim 1, wherein the pH-sensitive fluorescent dye comprises carboxy SemiNapthoRhodaFluor-1 acetoxymethyl ester, acetate.

5. The method of claim 1, wherein the $Na^+/H^+$ exchanger inhibitor is 5-(N, N hexamethylene)-amiloride (HMA).

* * * * *